(12) United States Patent
Cordray

(10) Patent No.: US 7,541,052 B1
(45) Date of Patent: Jun. 2, 2009

(54) HYPERTONIC SOLUTIONS AND METHOD OF TREATMENT

(76) Inventor: Scott Cordray, 725 Country Woods Way, Sapulpa, OK (US) 74066

( * ) Notice: Subject to any disclaimer, the term of this patent is extended or adjusted under 35 U.S.C. 154(b) by 0 days.

(21) Appl. No.: 11/318,288

(22) Filed: Dec. 23, 2005

(51) Int. Cl.
*A61K 33/14* (2006.01)

(52) U.S. Cl. .................. 424/678; 424/679; 424/681; 424/697

(58) Field of Classification Search .............. None
See application file for complete search history.

(56) References Cited

U.S. PATENT DOCUMENTS

| | | | |
|---|---|---|---|
| 5,466,680 A * | 11/1995 | Rudy | 514/57 |
| 5,869,497 A * | 2/1999 | Johnson et al. | 514/278 |
| 6,562,363 B1 * | 5/2003 | Mantelle et al. | 424/434 |
| 6,630,163 B1 * | 10/2003 | Murad | 424/464 |
| 6,641,799 B2 * | 11/2003 | Goldberg | 424/45 |
| 6,664,289 B2 * | 12/2003 | Hansen | 514/494 |
| 2003/0072828 A1 * | 4/2003 | Harrison et al. | 424/776 |

FOREIGN PATENT DOCUMENTS

| | | | |
|---|---|---|---|
| CN | 152428 A | * | 9/2004 |
| WO | WO 01/00218 | * | 4/2001 |

OTHER PUBLICATIONS

Talbot et al. "Mucociliary Clearance and Buffered Hypertonic Saline Solution," Laryngosocpe 107:Apr. 1997; 500-503, (4 pages total).*
Counsell, A. "The Dead Crystals," May/Jun. 1986, vol. 37, No. 3. (3 pages total).*
http://www.drugs.com/pro/lactated-ringer-s.html—accessed Nov. 6, 2007.*

* cited by examiner

*Primary Examiner*—Susan C Hoffman
(74) *Attorney, Agent, or Firm*—John Lezdey & Assoc

(57) ABSTRACT

The present invention provides hypertonic solutions for treating irritations and inflammations of the nasal passageways. The solutions contain magnesium salts and calcium salts.

6 Claims, No Drawings

HYPERTONIC SOLUTIONS AND METHOD OF TREATMENT

FIELD OF THE INVENTION

The present invention relates to the treatment of irritations and inflammations of the nasal passageways and cavity. More particularly, there is provided a hypertonic solution of inorganic salts that prevents the degranulation of mast cells, inhibits the release of arachadonic acid and 5-lipoxygenase enzyme and irrigates the nasal passageways.

BACKGROUND OF THE INVENTION

Allergic rhinitis, sinusitis, and epistaxis, as well as common irritations, can each be induced by any one of smoke, chemicals, pollens, mold or dust mites. Pollens cause the release of serine proteases such as tryptase and chymase and the activation of IgE which causes the degranulation of mast cells so as to initiate the acute inflammatory cycle. Mast cells release histamines release factors. Through a number of mechanisms the results can be itchy nose, rhinorrhea and itchy and watery eyes. Inflammation by smoke or chemicals can cause the release of arachadonic acid as well as leukotriene B4. Dust mites are known to increase the amount of eosinophiles in asthma patients. Steroids such as triamcinolone acetonide have been commonly used to treat the symptoms. However, there are problems associated with prolonged use of steroids. More particularly, steroid use by children has been discouraged because nasal sprays will cause swallowing by children so that side effects may result. The use of antihistamines does not solve the inflammation resulting from mast cell degranulation and cannot be used over prolonged periods.

Trypsin which is released by mast cells triggers the release of proteinase activating factors (PARS) especially PAR-2 which has a role in inflammation and inducing arachadonic acid release. Cromolyn inhibits the activation of PAR-2 and aids in the prevention of the degranulation of mast cells.

Since any different number of factors are involved in causing nasal irritations and inflammations, it would be preferable to have a method of treatment which can reduce the allergens or irritants in the nasal passageways that can be used over long periods of time as well as treat any inflammations that can be used by children as well as adults.

U.S. Pat. No. 6,562,363 to Mantelle et al discloses a bioadhesive for treating mucos membranes including nasal micosa membranes with cromolyn and bromide salts. However, hypertonic solutions are considered to be preferable as presently claimed.

U.S. Pat. No. 5,466,680 to Rudy discloses a gel composition containing magnesium and calcium cations for use in mucosal or cutaneons surfaces for enhancing white blood cells which included dextrose and dextran which has a viscosity of 2.5 centipoise and with carboxymethyl cellulose so that the viscosity is 3.5 centipoise, a hypertonic solution is not disclosed.

U.S. Pat. No. 6,630,163 discloses a composition for treating dermatological conditions with a zinc component and myrrh which are used in combination with fruit extracts. No mention is mentioned with regard to nasal inflammations or the use of inorganic bromide salts.

Anderson et al in the article entitled, "Hypertonic saline increases secretory and exudative responses of human nasal airways in vivo", Eur. Resp. Journal, 21(2) 308-12, February 2003 discloses that hypertonic saline irrigation solutions such as Ringer's lactate are effective but have pro-inflammatory properties that induces mucus and causes hypersecretion.

SUMMARY OF THE INVENTION

There is provided a hypertonic composition and method for treating the symptoms associated with the irritation and inflammation of nasal passages and nasal cavity caused by allergens and irritants which cause the release of histamine, arachadonic acid and serine proteases. More particular, there is provided a method for irrigating and treating the nasal passageways with a hypertonic composition comprising
  a) about 1 to 10 percent by weight of salts comprising
    1) about 45 to 60% by weight of magnesium chloride,
    2) about 29 to 41% by weight of potassium chloride, and
    3) about 1 to 5% by weight of salts selected from the group consisting of magnesium bromide, calcium chloride, calcium bromide, sodium bromide and magnesium sulfate,
  b) the remainder being water.

The composition is buffered to a pH of about 6.0 to 7.5.

The composition may include plant extracts especially for irrigation and as a decongestant.

Advantageously, the composition contains about 1 to 5% by weight of salts selected from the group consisting of magnesium bromide, calcium chloride, calcium bromide, sodium bromide and magnesium sulfate (Epsom salts).

It is further advantageous to include in the composition cromolyn, which is a PAR-2 inhibitor.

It is therefore an object of the invention to provide a method and composition for the treatment of irritations and inflammations of the nasal passageways with a hypertonic solution comprising magnesium and potassium chloride.

It is another object of the invention to reduce the presence of allergen and irritants in the nasal passageways by irrigation with a hypertonic aqueous composition comprising inert salts.

It is yet another object of the invention to prevent the degranulation of mast cells and to inhibit the release of arachadonic acid and histamine.

DESCRIPTION OF THE PREFERRED EMBODIMENTS

The present invention relates to a method and composition for treating a patient suffering from an irritation and/or inflammations of the nasal passageway and cavity. More particularly, there is provided a method and composition of nasally administering an effective amount of an aqueous hypertonic composition comprising:
  A) about 1 to 10% by weight, preferably about 1 to 5% by weight of salts comprising:
    1) about 45 to 60% by weight of magnesium chloride, preferably about 55 to 58%.
    2) about 29 to 41% by weight of potassium chloride, preferably about 39 to 40%,
    3) about 0.4 to 5% by weight of salts selected from the group consisting of magnesium bromide, calcium chloride, calcium bromide, sodium bromide and magnesium sulfate, and
  B) the remainder water, the composition being buffered to a pH of about 6.0 to 7.5, whereby the irritation and/or inflammation is reduced.

The buffer can comprise a buffer selected from the groups comprising sodium phosphate, potassium phosphate, sodium carbonate and the like as is commonly used by those skilled in the art.

The aqueous composition may include cromolyn in an amount of about 0.5 to 4%, preferably 0.5 to 1%, to further inhibit the degranulation of mast cells and also inhibit the activation of arachadonic acid caused by irritants.

Zinc ions, such as in the form of zinc gluconate, have been found useful when viruses are involved and can be used in amounts up to 2%.

Plant extract can be included such as echinacea which has been reported to inhibit gram-negative bacteria, Myrrh oil from cammphora abyssinica which helps to fight infection, and terpenes such as eucalyptus which is antiviral and aids in decongestion. The plant extracts can be used in amounts of about 0.5 to 2% by weight.

The zinc ions and the plant extracts are particularly useful in irrigating the nasal passageways to reduce the allergens or irritants and when a viral infection is suspected.

Optionally, the composition can contain up to 4% sodium chloride.

A preferred 100 ml composition of the present invention comprises:

| Ingredient | Wt. |
|---|---|
| Magnesium Chloride | 1.0-2.00 g |
| Magnesium Bromide | 0.01-0.05 |
| Magnesium Sulfate | 0.01-0.05 |
| Potassium Chloride | 0.8-1.00 g |
| Calcium Chloride | 0-0.05 g |
| Sodium Carbonate | 0-0.05 g |
| 1% Saline Solution | q.s. |

Optionally about 0.1 g of cromolyn may be added.

The pharmaceutical compositions may be prepared for nasal administration according to standard formulating procedures.

The salts may be dissolved in sterile water, physiological saline solution or buffer solution with a pH of 6.5 to 7.5 which is advantageously ionically balanced. For example, the preferred formulation for borax buffer is as follows:

Solution A-1.9 g $Na_2P_4O_7$ per 100 ml of $H_2O$.

Solution B-1.25 g $H_3BO_3$+0.3 g NaCl per 100 ml $H_2O$ is mixed with Solution A and the salts are added.

It is preferred to include a preservative, for example, Thimerosal or benzalkonium chloride and/or an antioxidant, for example, vitamin E. Other filler materials which can be included and are commonly found in nasal compositions as long as the composition remains hypertonic.

The compositions are generally administered every four to eight hours and/or as conditions of the patient and atmosphere require.

The following examples further illustrate the practice of this invention, but are not intended to be limiting thereof. It will be appreciated that the selection of actual amounts of composition to be administered to any individual patient will fall within the discretion of the attending physician and will be prescribed in a manner commensurate with the appropriate dosages will depend on the stage of the disease and like factors uniquely within the purview of the attending physician.

Example 1

A hypertonic solution which is effective as a nasal spray or nose drops is prepared as follows:

| Ingredient | % Weight |
|---|---|
| Magnesium Chloride | 1.0 mg |
| Potassium Chloride | 1.0 mg |
| 10% Saline Solution | 97.9 |
| Anti-oxidant | 0.1 mg |

The solution may additionally include 0.5% of calcium chloride and 0.5% of magnesium bromide.

The solution is effective to treat nasal irritations.

Example 2

A 10 ml hypertonic solution which is effective as a nasal spray or nose drops is prepared as follows:

| Ingredient | Wt. |
|---|---|
| Magnesium Chloride | 0.30 mg |
| Magnesium Bromide | 0.05 mg |
| Magnesium Sulfate | 0.05 mg |
| Potassium Chloride | 0.3 mg |
| Potassium sorbate solution | 10.0 mg |
| Vitamin E | 0.01 mg |
| Purified Water | q.s. |

The solution is buffered to a pH of about 7.0.

Optionally, about 0.05 mg of cromolyn may be added.

Example 3

A 100 ml hypertonic solution is prepared by admixing the following:

| Ingredient | Wt. gm |
|---|---|
| Magnesium Chloride | 2.00 |
| Magnesium Bromide | 0.05 |
| Magnesium Sulfate | 0.05 |
| Potassium Chloride | 1.00 |
| Calcium Chloride | 0.05 |
| Sodium Carbonate | 0.05 |
| 1% Saline Solution | q.s. |

Example 4

Forty-two patients were treated with either Ringer's lactate saline (n–20) or the hypertonic solution of Example 3 for a four week period.

Rhinitis symptom scores based on the severity (0=no discomfort to 3=severe discomfort) of 16 individual symptoms were totaled to obtain composite scores for baseline (prior to initiating treatment) and after 4 continuous weeks of treatment. The mean baseline symptom score for the hypertonic saline group was 14.9±6.9 versus 17.4+8.4 for the group of Example 4 solution. There was no difference between these values (P=0.312). However, after four weeks of treatment, the mean symptom score for the hypertonic saline was 15.2±8.6; this value was not different from baseline (P=0.851). In contrast, the mean symptom score for the group of Example 3 solution decreased significantly to 7.7±5.9 (P<0.001). The Example 3 solution group mean composite rhinitis symptom score at 4 weeks was significantly lower than the 4-week score in the hypertonic saline patients (P=0.003). Twenty-one of 22 patients (95.5%) treated with solution of Example 3 for 4 weeks demonstrated improved mean composite rhinitis scores as compared with 12 of 20 patients (60%) of patients treated with 4 weeks of hypertonic saline.

The RQLQ(S) scores based on the "how troubled you have been during the last week as a result of your nose/eye symptoms" (0=Not troubled to 6=Extremely troubled) of 28 individual questions categorized into seven (7) domains were totaled to obtain composite scores for baseline (prior to initiating treatment) and after 4 continuous weeks of treatment. The mean baseline RQLQ(S) score for the hypertonic saline group was 63.5±36.7 versus 80.3±34.9 for the Example 3 solution group. There was no difference between these values (P=0.137). However, after four weeks of treatment the mean symptom score for the hypertonic saline was 64.1±36.1; this value was not different from baseline (P=0.915). In contrast, the mean symptom score for the Example 4 solution group decreased significantly to 25.2±13.7 (P<0.001). The Example 3 solution group mean composite rhinitis symptom score at 4 weeks was significantly lower than the 4-week score in the hypertonic saline patients (P<0.001). All 22 patients (100%) treated with Example 3 solution for 4 weeks demonstrated improved mean composite RQLQ(S) scores as compared with 8 of 20 patients (40%) of patients treated with 4 weeks of hypertonic saline.

Regarding the individual RQLQ(S) domains, the mean baseline (prior to initiating treatment) scores were not different for Activity, Sleep, Non-Nose/Eye symptoms, Eye symptoms and Emotional domains. The baselines scores for Practical Problems and Nasal symptoms were both significantly higher (more troubling) in the Example 3 solution patients as compared to the hypertonic saline patients (10.2±4.9 versus 6.5+3.7 for Practical Problems and 13.3±5.1 vs. 9.7±5.1 for Nasal Symptoms) After 4 weeks of continuous treatment with either hypertonic saline or Example 3 solution, all individual RQLQ(S) domain mean scores were significantly lower in the Example 3 solution patients as compared to the hypertonic saline patients.

What is claimed:

1. A method of treating a patient suffering from inflammation and/or irritation of the nasal passageways which comprises nasally administering an effective amount of an aqueous hypertonic composition consisting essentially of:
   A) about 1 to 10% by weight of salts consisting essentially of:
      1) about 45 to 60% by weight of magnesium chloride;
      2) about 29 to 40% by weight of potassium chloride, and
      3) about 0.4 to 5% by weight of salts selected from the group consisting of magnesium bromide, calcium chloride, calcium bromide, sodium bromide and magnesium sulfate,
   B) the remainder being water, whereby mucus secretion is induced and the irritation or inflammation is reduced.

2. The method of claim 1 wherein said aqueous hypertonic composition is buffered at about pH 6.0 to 7.5.

3. The method of claim 1 wherein said patient is suffering from allergic rhinitis.

4. The method of claim 1 wherein a 100 ml of said aqueous hypertonic composition consists of:

| Ingredient | Wt. |
| --- | --- |
| Magnesium Chloride | 1.0-2.00 g |
| Magnesium Bromide | 0.01-0.05 g |
| Magnesium Sulfate | 0.01-0.05 g |
| Potassium Chloride | 0.08-1.00 g |
| Calcium Chloride | 0-0.05 g |
| Sodium Carbonate | 0-0.05 g and |
| Purified Water | as much as sufficient. |

5. The method of claim 4 wherein the hypertonic composition is buffered at pH 6.0-7.5.

6. A method of treating a patient suffering from inflammation and/or irritation of the nasal passageways which comprises nasally administering an effective amount of a buffered aqueous hypertonic composition consisting essentially of:
   A) about 1 to 10% by weight of salts consisting essentially of;
      1) about 45 to 60% by weight of magnesium chloride;
      2) about 29 to 40% by weight of potassium chloride;
      3) about 1 to 5% by weight of magnesium bromide, and
   B) water
   whereby mucus secretion is induced and the inflammation is reduced.

* * * * *